(12) United States Patent
Kim et al.

(10) Patent No.: US 11,186,612 B2
(45) Date of Patent: Nov. 30, 2021

(54) SUBSTANCE P ANALOG HAVING PROGENITOR CELL OR STEM CELL RECRUITING ACTIVITY AND METHOD FOR PROGENITOR CELL OR STEM CELL RECRUITING USING THE SAME

(71) Applicant: AJOU UNIVERSITY INDUSTRY-ACADEMIC COOPERATION FOUNDATION, Suwon-si (KR)

(72) Inventors: Moon Suk Kim, Suwon-si (KR); Sang Dun Choi, Suwon-si (KR); Seung Hun Park, Seoul (KR); Masaud Shah, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/858,071

(22) Filed: Apr. 24, 2020

(65) Prior Publication Data

US 2020/0299330 A1 Sep. 24, 2020

(30) Foreign Application Priority Data

Feb. 25, 2019 (KR) .................. 10-2019-0021522

(51) Int. Cl.
*A61K 38/08* (2019.01)
*A61K 38/00* (2006.01)
*A61P 17/02* (2006.01)
*C07K 7/06* (2006.01)
*C07K 7/22* (2006.01)

(52) U.S. Cl.
CPC ............... *C07K 7/06* (2013.01); *A61P 17/02* (2018.01); *A61K 38/00* (2013.01)

(58) Field of Classification Search
CPC ...... A61K 38/00; A61K 38/046; A61K 38/08; A61P 17/02; C07K 7/06; C07K 7/22
See application file for complete search history.

(56) References Cited

U.S. PATENT DOCUMENTS

2010/0081182 A1* 4/2010 Paul .................... C12P 7/16
435/160

* cited by examiner

*Primary Examiner* — Julie Ha
(74) *Attorney, Agent, or Firm* — Sughrue Mion, PLLC

(57) ABSTRACT

A substance P analog having a progenitor cell or stem cell recruiting activity and a method of recruiting progenitor cells or stem cells using the substance P analog are disclosed. The substance P analog has an effect of recruiting endogenous progenitor cells or stem cells to a wound or disease-occurring site. Thus, the disclosure also describes its use in recruiting progenitor cells or stem cells and a method of regenerating or treating a damaged organ or tissue, or a method of healing a wound.

6 Claims, 8 Drawing Sheets

Specification includes a Sequence Listing.

SUBSTANCE P ANALOG HAVING PROGENITOR CELL OR STEM CELL RECRUITING ACTIVITY AND METHOD FOR PROGENITOR CELL OR STEM CELL RECRUITING USING THE SAME

This application was supported by the National Research Foundation of Korea (No. 2019051471).

CROSS-REFERENCE TO RELATED APPLICATION

This application claims priority to and the benefit of Korean Patent Application No. 10-2019-0021522, filed on Feb. 25, 2019, the disclosure of which is incorporated herein by reference in its entirety.

BACKGROUND

1. Field of the Invention

The present invention relates to a substance P analog having a progenitor cell or stem cell recruiting activity and a method of recruiting progenitor cells or stem cells using the same, and more particularly, to a substance P analog having an effect of recruiting endogenous progenitor cells or stem cells to a wound or disease-occurring site and a method of recruiting progenitor cells or stem cells using the same, a method of regenerating or treating a damaged organ or tissue, or a method of healing a wound.

2. Discussion of Related Art

Mesenchymal stem cells (MSCs), which are adult stem cells, have self-regenerating ability and multipotency capable of differentiating into a variety of mesenchymal tissue, including bone, fat and cartilage. In addition, such MSCs help in healing a disease due to tropism allowing movement to damaged tissue and an inflammatory site, and exhibit an immunosuppressive property under various conditions. However, there is a problem of expressing a relatively small amount of chemokine receptors and factors for stem cells to be moved to a disease site, and to this end, stem cell-inducing factors are needed.

Conventionally reported substance P (SP) is a neuropeptide of 11 amino acids (Arg-Pro-Lys-Pro-Gln-Gln-Phe-Phe-Gly-Leu-Met-NH$_2$) (SEQ ID NO: 2) playing a role in neurotransmission and neuromodulation, and an endogenous receptor for SP is neurokinin 1 receptor (NKR1), which belongs to the tachykinin receptor subfamily of G-protein-coupled receptors. NKR1 is distributed in various cell types (neurons, glia cells, capillaries, lymph nodes, fibroblasts, stem cells and white blood cells) in a variety of tissue and organs, and SP is one of stem cell recruiting factors, which amplify or activate most cell signaling processes and are well studied.

Therefore, in the present invention, to prepare a peptide having a progenitor and/or stem cell recruiting activity, a SP analog, which is an NKR1-binding peptide ligand, was selected using an interface structure of SP and NKR1, and it was confirmed that the selected SP analog has an excellent stem cell recruiting activity, compared with the conventional SP, and thus the present invention was completed.

SUMMARY OF THE INVENTION

The present invention is directed to providing a substance P (SP) analog having a progenitor cell or stem cell recruiting activity.

The present invention is also directed to providing a method of recruiting progenitor cells or stem cells using a SP analog.

The present invention is also directed to providing a method of regenerating or treating a damaged organ or tissue and a method of healing a wound using a SP analog.

In one aspect, the present invention provides a polypeptide which has a progenitor cell or stem cell recruiting activity and includes an amino acid sequence of SEQ ID NO: 1.

In an exemplary embodiment of the present invention, the polypeptide may be a SP analog.

In another exemplary embodiment of the present invention, the progenitor cells or stem cells may be endogenous progenitor cells or endogenous stem cells.

In still another exemplary embodiment of the present invention, the endogenous stem cells may be one or more selected from the group consisting of mesenchymal stem cells (MSCs), corneal stem cells, myocardial stem cells, auditory stem cells and neural stem cells, and preferably, MSCs.

In another aspect, the present invention provides a method of recruiting progenitor cells or stem cells in a subject, which includes moving progenitor cells or stem cells in a subject by administering an effective amount of a composition including a polypeptide having an amino acid of SEQ ID NO: 1 to a subject.

In still another aspect, the present invention provides a method of regenerating or treating a damaged organ or tissue of a subject, which includes moving progenitor cells or stem cells to a damaged organ or tissue by administering an effective amount of a composition containing a polypeptide having an amino acid of SEQ ID NO: 1 to a damaged organ or tissue of a subject.

In yet another aspect, the present invention provides a method of healing a wound, which includes moving progenitor cells or stem cells to a damaged site by administering an effective amount of a composition containing a polypeptide having an amino acid of SEQ ID NO: 1 to a damaged site of a subject.

In yet another aspect, the present invention provides a method of treating a disease, which includes moving progenitor cells or stem cells to a diseased site by administering an effective amount of a composition containing a polypeptide having an amino acid of SEQ ID NO: 1 to a subject, wherein the disease is a skin disease, a brain nervous system disease, a cardiovascular disease, a digestive system disease, a respiratory disease, a urinary system disease, a motor-related disease, a vascular disease, an endocrine disease, a hearing disease or an ophthalmic disease.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
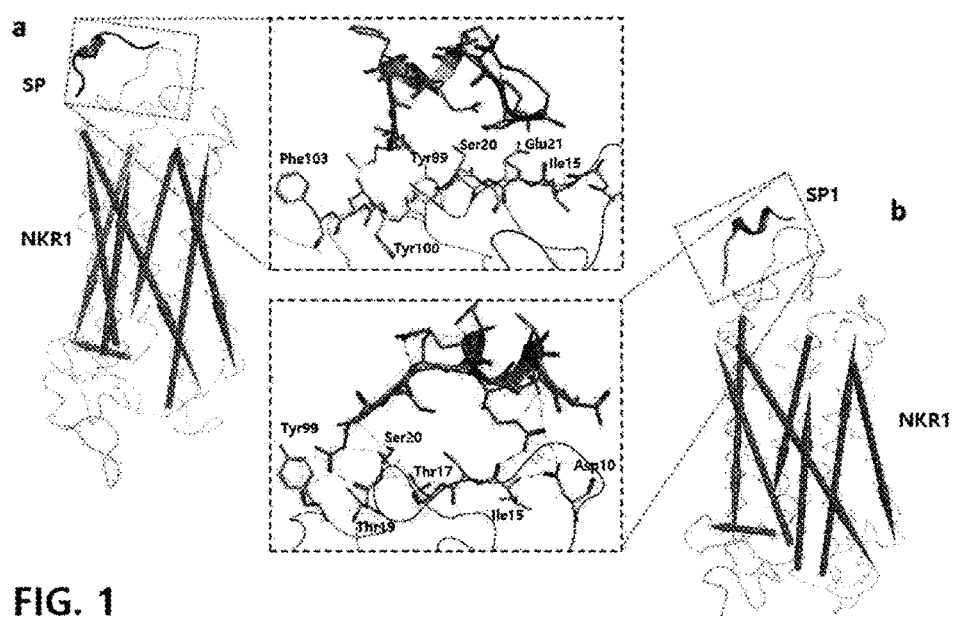
FIG. 1 is a schematic diagram of analyzing an interface (a) between substance P (SP) and neurokinin 1 receptor (NKR1) and an interface (b) between a substance P analog (SP1) of the present invention and NKR1.

Hereinafter, the present invention will be described in detail.

In one aspect, the present invention relates to a polypeptide having a progenitor cell or stem cell recruiting activity and including an amino acid sequence of SEQ ID NO: 1.

In the present invention, the polypeptide may be a substance P analog (also referred to as SP1).

Substance P (also referred to as "SP") is one of mammalian tachykinins, composed of a sequence of 11 amino acids such as RPKPQQFFGLM (SEQ ID NO: 2), and a substance which is excessively released when tissue is wounded, and has a capability of inducing recruiting (capture or promotion of movement) of multipotent stem cells for wound healing. In the present invention, to prepare a peptide having a higher stem cell recruiting activity, SP1 represented by an amino acid sequence of SEQ ID NO: 1 was selected using the structure of an interface between SP and neurokinin 1 receptor (NKR1).

In the present invention, the progenitor cells or stem cells may be endogenous cells, which are one or more selected from the group consisting of mesenchymal stem cells (MSCs), corneal stem cells, myocardial stem cells, auditory stem cells, nerve stem cells and vascular endothelial progenitor cells, and preferably MSCs.

Endogenous progenitor cells or endogenous stem cells are originally present in a specific organ and/or tissue, and when a corresponding organ and/or tissue is damaged, they refer to cells having self-replicating ability and multipotency, contributing to the regeneration of the tissue and/or organ. A specific example of the endogenous progenitor or stem cells may be MSCs, corneal stem cells, myocardial stem cells, auditory stem cells, nerve stem cells or vascular endothelial progenitor cells.

The progenitor cell or stem cell recruiting activity promotes the movement of progenitor cells or stem cells, which means that progenitor cells or stem cells flow in blood circulating from the bone marrow, organ and/or tissue; accumulate in a damaged organ and/or tissue from the circulating blood; or move into the organ and/or tissue.

In addition, the polypeptide having a progenitor cell or stem cell recruiting activity of the present invention may not only promote a recruiting activity (promotion of movement), but also promote the proliferation or differentiation of progenitor cells or stem cells.

In an exemplary embodiment of the present invention, SP1, which is an NKR1-binding peptide ligand capable of optimally activating a receptor, was selected using the structure of an interface between SP and NKR1, which is an endogenous receptor for SP and known to be distributed in stem cells, and a computer simulation system. As shown in Table 1, the selected SP1 in the present invention is composed of a sequence of 11 amino acids, RISPQQRDALA (SEQ ID NO: 1).

In another exemplary embodiment of the present invention, to compare stem cell recruiting activities between SP and SP1 of the present invention, stem cell migration was evaluated in an ex vivo environment. As a result, as shown in FIG. 2(*a*) and FIG. 2(*b*), it was confirmed that the stem cell migration of SP1 increases, compared with that of SP.

Recently, while stem cell therapeutics have attracted attention as therapeutic agents for various diseases, a method of introducing stem cells from an external environment of a patient has a risk of complications caused by excessive regeneration and/or excessive repair of transplanted cells. On the other hand, a method using "self-regeneration" may regenerate a damaged organ and/or tissue by activating stem cells originally present in the body of a patient.

Since a polypeptide having a stem cell recruiting activity of the present invention has an effect of moving stem cells to a tissue or wound site required for regeneration, it may be used in progenitor cell or stem cell recruiting, regeneration or treatment of an organ and/or tissue, or wound healing.

Accordingly, in another aspect, the present invention provides a method of recruiting progenitor cells or stem cells in a subject, which includes moving progenitor cells or stem cells in a subject by administering an effective amount of a composition including a polypeptide having an amino acid of SEQ ID NO: 1 to a subject.

In still another aspect, the present invention provides a method of regenerating or treating a damaged organ or tissue of a subject, which includes moving progenitor cells or stem cells to a damaged organ or tissue by administering an effective amount of a composition including a polypeptide having an amino acid of SEQ ID NO: 1 to the damaged organ or tissue of a subject in need of treatment.

In yet another aspect, the present invention provides a method of healing a wound, which includes moving progenitor cells or stem cells to a wound site by administering an effective amount of a composition including a polypeptide having an amino acid of SEQ ID NO: 1 to the wound site of a subject in need of treatment.

In yet another aspect, the present invention provides a method of treating a disease, which includes moving progenitor cells or stem cells to a diseased site by administering an effective amount of a composition including a polypeptide having an amino acid of SEQ ID NO: 1 to a subject in need of treatment, wherein the disease is a skin disease, a brain nervous system disease, a cardiovascular disease, a digestive system disease, a respiratory disease, a urinary system disease, a motor-related disease, a vascular disease, an endocrine disease, a hearing disease or an ophthalmic disease.

The "subject" indicates any animal, such as a mammal, a bird, an ape, a dog, a cat, a horse, a cow, or a rodent. The mammals include humans and other mammals except a human.

The "effective amount" refers to an amount of a polypeptide sufficient for achieving a desired effect in a subject to be treated or a composition containing the polypeptide. For example, the effective amount may be an amount effective for increasing recruiting of progenitor cells or stem cells, which is required to treat or regenerate a wound site, or a damaged tissue/organ. The effective amount may vary according to a physical condition (e.g., an age, a gender, the type and stage of a disease, a general physical condition, reactivity to a given dose, or a desired clinical effect) of a subject and an administration route.

The "treatment" refers to both of therapeutic treatment and a preventive action for preventing or reducing a targeted disease or disorder even though treatment eventually fails. A subject in need of treatment may include not only a subject already suffering from a disease, but also a subject prone to a disease or subject with a disease to be prevented.

In the method of the present invention, the progenitor cells or stem cells are endogenous progenitor cells or endogenous stem cells, but special progenitor cells or stem cells may be administered to a subject as needed.

In the method of the present invention, substance P or an analog thereof having a stem cell recruiting activity, an NKR1-binding peptide ligand or a substance known to have a stem cell recruiting ability may be mixed with SP1, which is a polypeptide having an amino acid sequence of SEQ ID NO: 1, and progenitor cells or stem cells may be mixed as needed.

In the method of the present invention, the polypeptide (SP1) having the amino acid sequence of SEQ ID NO: 1 may be prepared in a hydrogel of a natural bio-substance which physically or chemically includes SP1 and administered, but the present invention is not limited thereto, and any method of administering a peptide known in the art may be used without limitation.

Specifically, a hydrogel of a natural bio-substance physically containing SP1 may be prepared by a method including:

i) preparing a first reaction solution in which a natural bio-substance to which a compound having a first chemical functional group is bound and a stem cell recruiting factor are mixed;

ii) preparing a second reaction solution in which a natural bio-substance to which a compound having a second chemical functional group is bound and a stem cell recruiting factor are mixed; and iii) mixing the first reaction solution prepared in Step i) and the second reaction solution prepared in Step ii).

In addition, a hydrogel of a natural bio-substance chemically containing SP1 may be prepared by a method including:

i) preparing a first reaction solution containing a natural bio-substance to which a compound having a stem cell recruiting factor and a first chemical functional group is bound;

ii) preparing a second reaction solution containing a natural bio-substance to which a compound having a stem cell recruiting factor and a second chemical functional group is bound; and iii) mixing the first reaction solution preparing in Step i) and the second reaction solution prepared in Step ii).

The "first chemical functional group" in Step i) is preferably any one selected from the group consisting of tetrazine, an alkyne group, an epoxy group and an acryloyl group, more preferably, tetrazine, but the present invention is not limited thereto.

The "second chemical functional group" in Step ii) is preferably any one selected from the group consisting of cyclooctene, an azide group, a thiol group and an amine group, and more preferably cyclooctene, but the present invention is not limited thereto.

More specifically, it is most preferable that the first chemical functional group and the second chemical functional group consist of the following combinations and are applied to prepare a hydrogel: (tetrazine and cyclooctene), (alkyne group and azide group), (alkyne group and thiol group), (epoxy group and amine group), (epoxy group and thiol group), (acryloyl group and amine group) or (acryloyl group and thiol group).

In addition, the "natural bio-substance" in Step i) or ii) may include a carboxyl group. The natural bio-substance including a carboxyl group may be bound to a compound containing a chemical functional group by an amide bond. Specifically, the natural bio-substance is preferably any one or more selected from the group consisting of hyaluronic acid, carboxymethyl cellulose (CMC) and alginate (AGNT), but the present invention is not limited thereto.

More preferably, when the natural bio-substance is hyaluronic acid, it may have a molecular weight of 500,000 to 6,000,000 Da. Here, when the molecular weight of the hyaluronic acid is less than 500,000 Da, physical properties may be too low to significantly form a hydrogel, and when the molecular weight of the hyaluronic acid is more than 6,000,000 Da, viscosity may increase to have a limitation on application as an injection formulation, but the present invention is not limited thereto.

The "binding" in Step i) or ii) may be performed by inducing a condensation reaction, preferably, an amide reaction, by additionally adding a condensing agent to a solution containing a natural bio-substance. The condensing agent may be 4-(4,6-dimethoxy-1,3,5-triazin-2-yl)-4-methylmorpholinium chloride (DMTMM), but the present invention is not limited thereto, and any condensing agent that can be understood to induce a condensation reaction with respect to a natural bio-substance by those of ordinary skill in the art may be applied without limitation. An amount of the condensing agent may be arbitrarily adjusted by those of ordinary skill in the art to control the extent of a condensation reaction.

Figure 3:
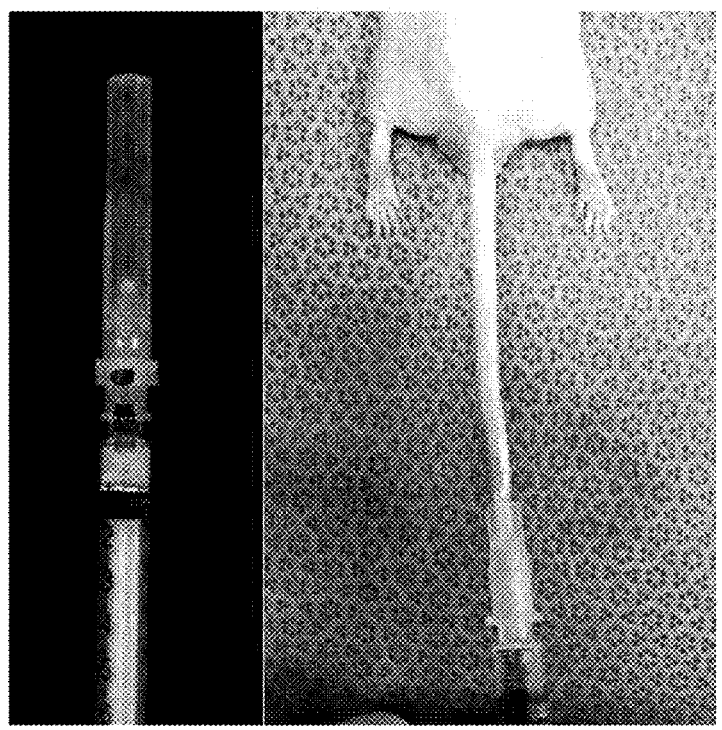
FIG. 3 is an image illustrating injection of human-derived MSCs labeled with indocyanine green into a mouse caudal vein.
Figure 4A:
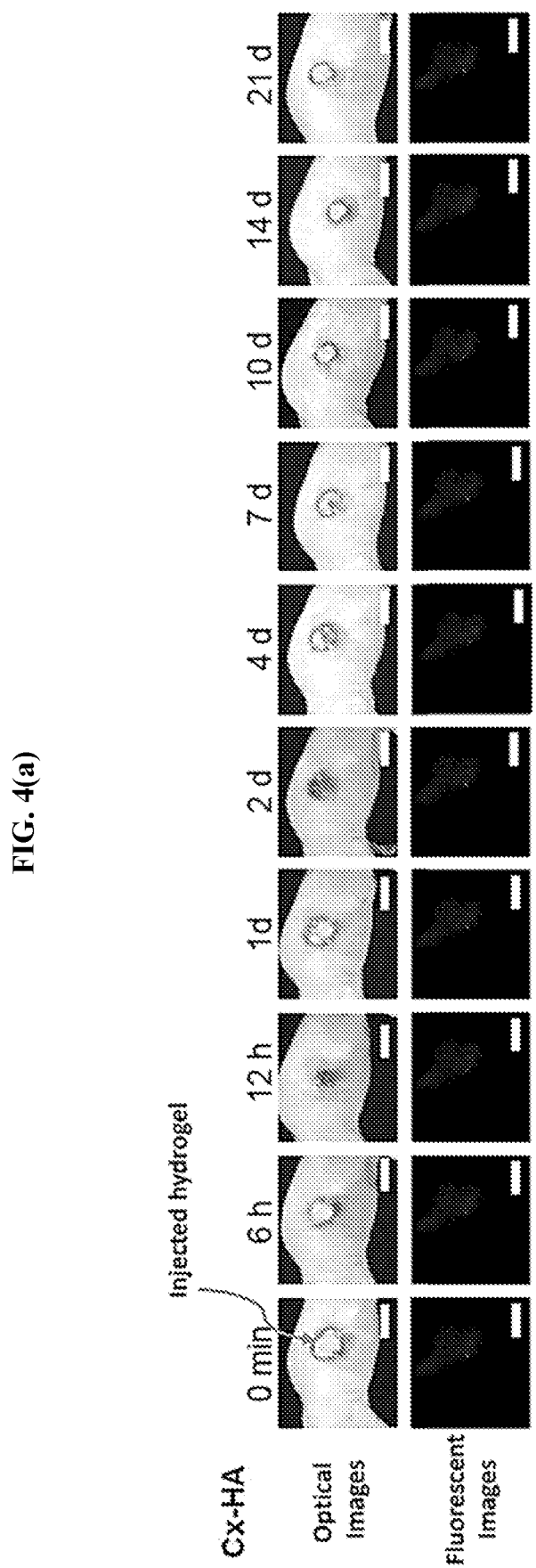
FIG. 4(*a*) and FIG. 4(*b*) are images showing the extent of stem cell migration over time when a hyaluronic acid hydrogel formulation containing SP is injected into one side of a mouse (Injected hydrogel: green, Recruited hMSC: red)
Figure 4B:
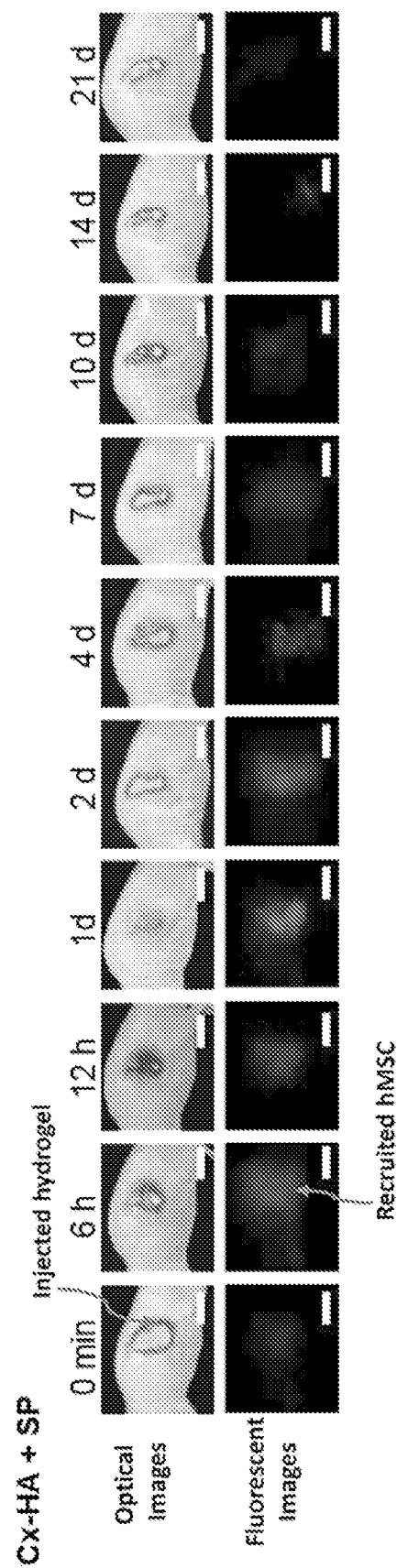
Figure 5:
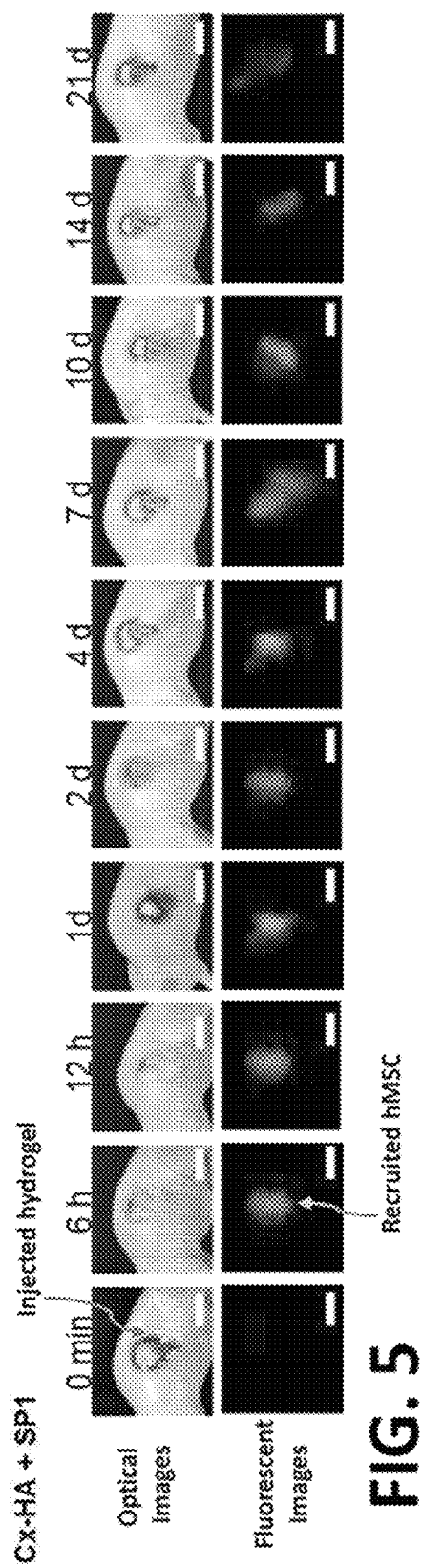
FIG. 5 is an image showing the extent of stem cell migration over time when a hyaluronic acid hydrogel formulation containing SP1 of the present invention is injected into one side of a mouse (Injected hydrogel: green, Recruited hMSC: red)

In an exemplary embodiment of the present invention, to confirm the stem cell recruiting activity of SP1 in vivo, a natural bio-substance physically containing SP or SP1 was prepared. Specifically, as shown in Example 3, a hyaluronic acid hydrogel (Cx-HA) formulation containing SP or SP1 was prepared, and injected into one side of a nude mouse. Human-derived MSCs were labeled with indocyanine green, and as shown in FIG. 3, injected into a mouse caudal vein. While fluorescence was not observed in a control (Cx-HA), in all experimental groups, fluorescence was observed only at an SP or SP1-injected site. As a result of comparing FIGS. 4(a) and 4(b) (SP) and 5 (SP1), it was confirmed that SP1 exhibits a higher stem cell recruiting activity, which is similar to the result of confirming stem cell migration in vitro.

Figure 6:
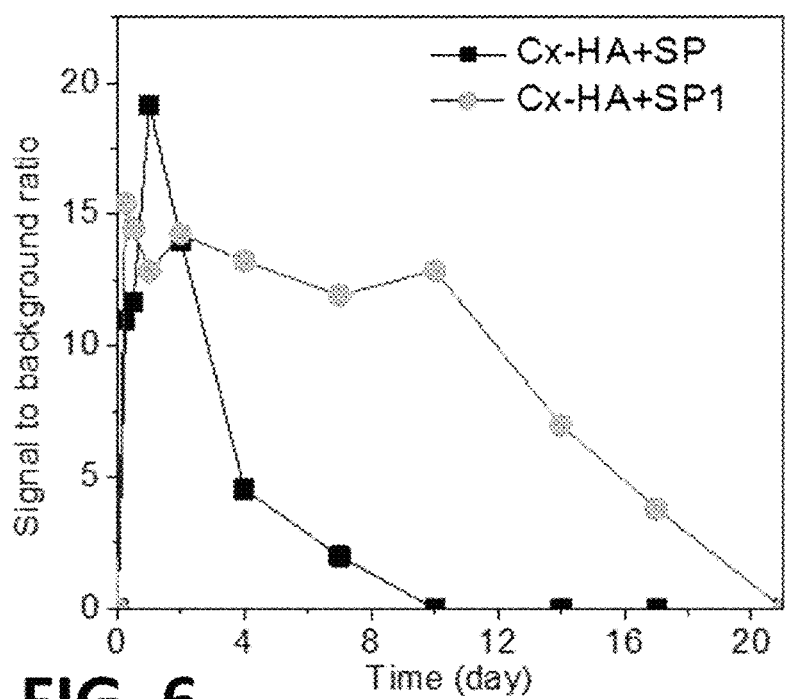
FIG. 6 shows data quantifying the extent of stem cell migration when hyaluronic acid hydrogel formulations containing SP and SP1 of the present invention, respectively, are injected into one side of a mouse.

In addition, as shown in FIG. 6, as a result of quantifying an amount of stem cells moved to a SP or SP1-injected site, it was confirmed that, compared with conventional SP, SP1 exhibits a higher stem cell recruiting activity, and also a stem cell recruiting activity maintenance time is longer.

That is, when the polypeptide (SP1) having the amino acid sequence of SEQ ID NO: 1 of the present invention was administered in vivo, since it was confirmed that, compared with conventional SP, stem cell recruiting efficiency is higher, the polypeptide having the amino acid sequence of SEQ ID NO: 1 of the present invention may be used in recruiting of progenitor cells or stem cells, regeneration or treatment of an organ and/or tissue, or wound healing.

An administration route of the polypeptide having the amino acid sequence of SEQ ID NO: 1 of the present invention or a pharmaceutical composition containing the same may be administered through a general route that can reach targeted tissue. The administration may be parenteral administration, for example, intraperitoneal administration, intravenous administration, intramuscular administration, subcutaneous administration or intradermal administration, but the present invention is not limited thereto. Here, to prepare the polypeptide in a formulation for parenteral administration, a solution or suspension was prepared by mixing a hydrogel containing a stem cell recruiting factor with a stabilizer or buffering agent in water, and may be prepared in a dosage unit of an ampoule or vial form. The composition may be sterilized and/or may contain a preservative, a stabilizer, a hydration agent or an adjuvant such as an emulsion accelerator, a salt for osmotic modulation and/or a buffering agent, and other therapeutically available substances, and may be prepared by a conventional method such as a mixing, granulating or coating method.

In addition, a dose of the polypeptide having the amino acid sequence of SEQ ID NO: 1 of the present invention or a pharmaceutical composition containing the same into the human body may vary according to the age, body weight and gender of a patient, an administration type, a health condition and the severity of a disease, and based on an adult patient with a body weight of 60 kg, the dose may be generally 0.001 to 1,000 mg/day, and preferably, 0.01 to 500 mg/day. The polypeptide or composition may be administered once to several times per day at regular intervals according to the judgment of a doctor or pharmacist.

The polypeptide having the amino acid sequence of SEQ ID NO: 1 of the present invention or pharmaceutical composition containing the same may be applied for a disease required for regeneration or treatment of an organ and/or tissue. Specifically, the disease may be a skin disease, a brain nervous system disease, a cardiovascular disease, a digestive system disease, a respiratory disease, a urinary system disease, a motor-related disease, a vascular disease, an endocrine disease, a hearing disease or an ophthalmic disease.

The skin disease may be one or more selected from the group consisting of a wound, a burn, a radiation disorder, frostbite, a UV disorder, an electric burn, a trauma, a skin ulcer, a bedsore, contact dermatitis, blistering dermatitis, atopic dermatitis, xeroderma, a diabetic skin ulcer, autosensitization dermatitis, erythroderma, exfoliative dermatitis, epidermolysis bullosa, photodermatitis, chronic pigmented purpura (Schamberg's disease), oral mucosal damage, stomatitis, perioral dermatitis, a skin aging symptom, hair loss, paronychia, an ingrown nail, the erosion of gastric mucosa, a digestive ulcer, corneal erosion, a corneal ulcer, caries, pulpitis, destructive periodontitis, allergic rhinitis, pollinosis, spring conjunctivitis, hemorrhoids, a digestive tract mucosal disorder, a digestive tract mucosal burn, bronchial asthma, glossitis, recurrent aphtha, aphthous stomatitis, halitosis, oral abnormal sensation, a dental infection, an oral mucosa bite, a tongue bite, an oral mucosa burn and an oral mucosal ulcer.

The brain nervous system disease may include one or more selected from the group consisting of stroke, Alzheimer's disease, Parkinson's disease, various central nervous system diseases (e. g, myelitis), various peripheral neuropathies (e.g., polyneuropathy), myelopathy and various types of encephalitis.

The cardiovascular disease may be one or more selected from the group consisting of myocardial infarction, angina, unstable angina, various types of myocarditis (e.g., viral myocarditis), acute heart failure, chronic heart failure, atherosclerosis, hypertension, rheumatic heart disease, arrhythmia, heart valve disease, infectious endocarditis, pericarditis, percutaneous coronary artery intervention, and restenosis and reocclusion after PTCA surgery.

The digestive system disease may include one or more selected from the group consisting of esophagitis, acute gastritis, chronic gastritis, a gastric ulcer, a duodenal ulcer, various types of colitis (e.g., ulcerative colitis), intestinal tuberculosis, viral hepatitis, alcoholic hepatitis, drug-induced hepatitis, fatty liver, sclerosis, pancreatitis, and organ disorders caused by surgery for various digestive cancers (e.g., liver cancer, colon cancer and stomach cancer).

The respiratory disease may include one or more selected from the group consisting of various types of bronchitis (e.g., bacterial bronchitis), infectious pneumonia, aspiration pneumonia, pulmonary embolism, pneumothorax and pulmonary dysfunction.

The urinary system disease may include one or more selected from the group consisting of cystitis, various types of nephritis (e.g., chronic nephritis syndrome and primary glomerular disease), adrenalitis, urethritis, bacterial and non-bacterial prostatitis, hypertensive nephropathy, diabetic nephropathy and renal failure.

The motor-related disease may include one or more selected from the group consisting of various types of arthritis (e.g., rheumatoid arthritis), muscle atrophy, a bone defect after craniotomy in neurosurgery, a bone defect after tumorectomy in orthopedic surgery, a bone defect after fracture, a bone defect caused by periodontitis in dentistry, chondritis, cartilage defects of various joints, and ligament damage caused by various types of damage (e.g., trauma and sprain).

The vascular disease may include one or more selected from the group consisting of various arterial diseases (e.g., arteriosclerosis obliterans (ASO) and thromboangiitis obliterans (TAO)), various venous diseases (e.g., thrombophlebitis), thrombosis, a hemodynamic disorder, deep vein thrombosis (DVT), various types of diseases associated with a peripheral circulation disorder (e.g., sudden sensorineural hearing loss and vibration disease), and restenosis and reocclusion after coronary angioplasty.

The endocrine disease may include one or more selected from the group consisting of diabetes and various complications (e.g., diabetic peripheral neurosis, diabetic foot, and diabetic ulcers), hyperlipidemia, thyroiditis and obesity.

The ophthalmic disease may include various types of keratitis (e.g., keratitis caused by an alkaline or acidic compound, and traumatic keratitis) or diabetic retinitis.

The hearing disease may include ototoxicity caused by various drugs (e.g., an anticancer agent, antipyretic, analgesic, antibiotic, etc.), noise-induced hearing loss, or senile deafness caused by aging.

Hereinafter, the present invention will be described in further detail with reference to examples.

The examples are merely provided to more fully describe the present invention, and it will be obvious to those of ordinary skill in the art that the scope of the present invention is not limited to the following examples.

Example 1

Selection of SP1 Having Excellent Stem Cell Recruiting Activity

In the present invention, an NKR1-binding peptide ligand, SP1, capable of optimally activating a receptor, was selected using an interface structure of NKR1, which is an endogenous receptor for SP and known to be distributed in stem cells, and SP and a computer simulation system.

Specifically, for structural analysis of SP and its receptor NKR1 (PDB ID; 2KSA, 20937248), a motif search package of the Molecular Operating Environment (MOE) program was used. The motif search package was used to search a protein database including a non-redundant dataset using information of a queried structure (e.g., SP), thereby collecting a secondary structure similar to SP.

A structural database of 80,000 types or less including 30,000 types or less of non-redundant chains were used in SP-associated motif selection. 12 types of motifs showing the highest scores were selected, and a protein-to-protein docking procedure was performed for analysis of affinity for NKR1. In each docking attempt, NKR1 was used as a receptor, and the SP group was used as a ligand, approximately 500 types of docking forms per SP were obtained using MOE program, and consistent docking types were selected based on Protein-Ligand Interaction Fingerprint (PLIF) in the MOE program.

As shown in Table 1, finally, an SP analog composed of the sequence of 11 amino acids RISPQQRDALA (SEQ ID NO: 1) was selected, and named "SP1."

TABLE 1

SP1 and SP sequence information

| Stem cell recruiting factor | Amino acid sequence | SEQ ID NO: |
|---|---|---|
| SP1 | RISPQQRDALA | 1 |
| Substance P (SP) | RPKPQQFFGLM | 2 |

In addition, as shown in FIG. 1, it was confirmed that SP1 interacts in a very similar form to SP interacting with NKR1, indicating that the SP1 of the present invention is highly likely to activate NKR1 and a downstream signal thereof.

Example 2

Evaluation of Stem Cell Migration of SP and SP1

In the present invention, to compare the stem cell recruiting activities of SP and the SP1 of the present invention, stem cell migration was evaluated in an ex vivo environment.

First, human-derived MSCs (hMSCs) were labeled with a PKH 26 dye (Sigma, USA), and 5×10$^4$ cells were put into an upper chamber (8.0 μm pore size) of a 24-well Transwell plate (SPL, Korea). After the hMSCs were cultured in the upper chamber for 48 hours using a serum-free DMEM (Gibco, USA), a medium prepared under the following conditions in Table 2 was added into a bottom well, and then the medium was replaced with a fresh one every third day, followed by observing hMSCs in the bottom well using a fluorescence microscope.

TABLE 2

Composition of medium containing stem cell recruiting factor

| Experimental Group | Medium Composition |
|---|---|
| Control | DMEM + 1% FBS |
| SP | DMEM + 1% FBS + 1 μg/mL SP |
| SP1 | DMEM + 1% FBS + 1 μg/mL SP1 |

Figure 2A:
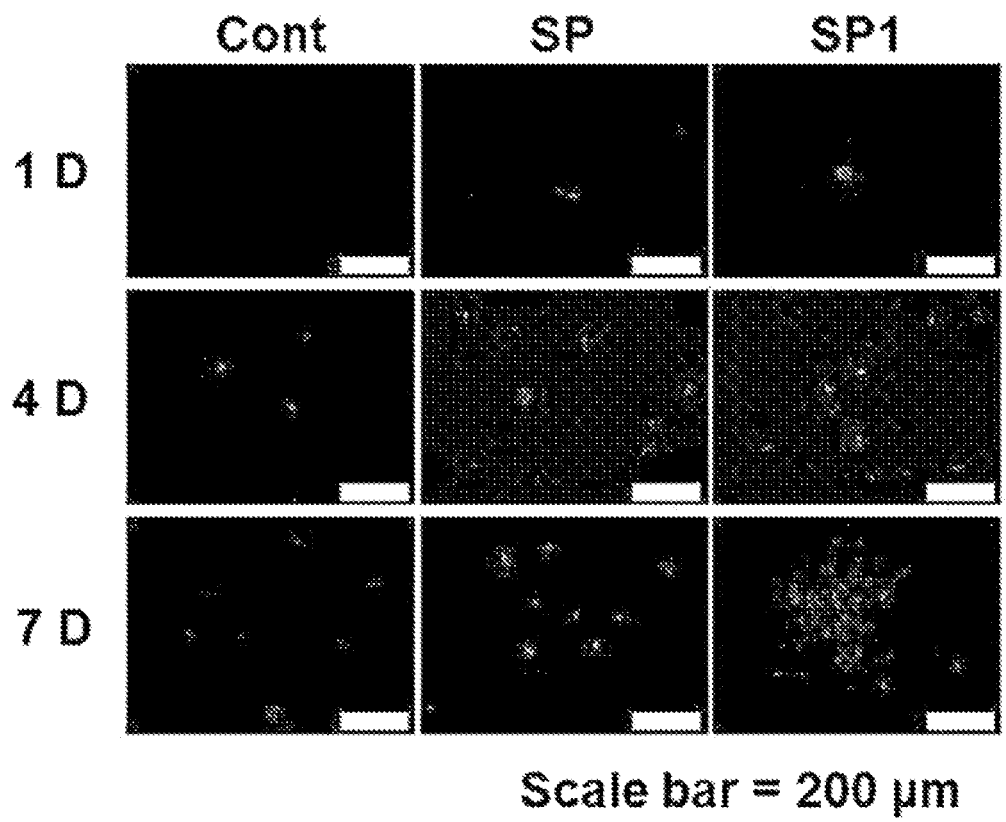
FIG. 2(a) and FIG. 2(b) show evaluation data for the stem cell migration of SP and SP1 of the present invention.
Figure 2B:
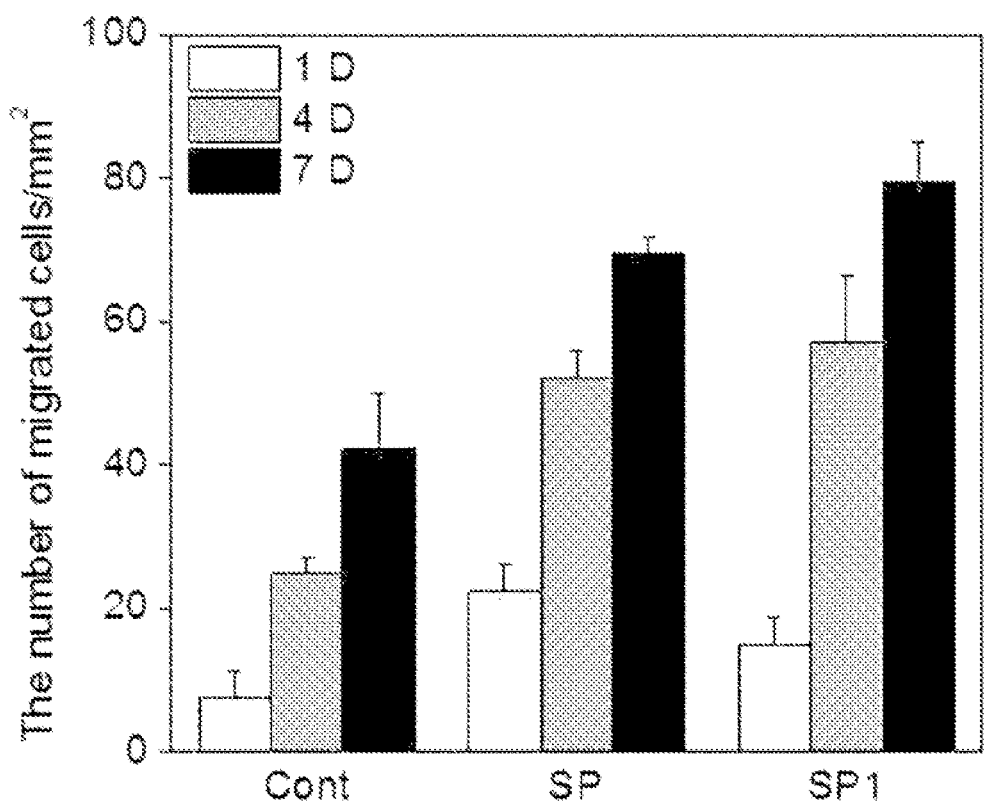

As a result, as shown in FIG. 2(a) and FIG. 2(b), it was confirmed that stem cells moved in the experimental group containing SP or SP1, compared with the control, and particularly, the number of moved stem cells is high in the SP1-treated group, compared with the SP-treated group.

Example 3

Preparation of Formulation Containing SP or SP1

3-1: Preparation of Crosslinking Agent-Introduced Hyaluronic Acid

A hyaluronic acid solution was prepared by adding 150 mg of hyaluronic acid (HA; molecular weight: 1,000,000 Da) to 15 mL of distilled water (DW), and stirring the resulting solution at 25° C. for 24 hours. 6 mL/vial of the solution was dispensed into two vials (60 mg of HA was dissolved in each vial).

Vial 1 (HA-Tet): 41.5 mg of 4-(4, 6-dimethoxy-1, 3, 5-triazine-2-yl)-4-methylmorpholinium chloride (DMT-MM) as a condensing agent and 11.9 mg of tetrazine (95.2 μL) were put into a hyaluronic acid solution, and reacted by stirring at 25° C. for 24 hours. Subsequently, the solution was concentrated by dialysis for 72 hours, and freeze-dried at −80° C., thereby preparing HA-TET in which TET was introduced into hyaluronic acid.

Vial 2 (HA-TCO): 41.5 mg of 4-(4, 6-dimethoxy-1, 3, 5-triazin-2-yl)-4-methylmorpholinium chloride (DMT-MM) as a condensing agent and 7.88 mg (63.04 μL) of trans-cyclooctene (TCO) were put into a hyaluronic acid solution, and reacted by stirring at 25° C. for 24 hours. Subsequently, the solution was concentrated by dialysis for 72 hours, and freeze-dried at −80° C., thereby preparing HA-TCO in which TCO was introduced into hyaluronic acid.

Next, to observe the hydrogel imaging, IR-783 dye was used to prepare NIR-labeled-HA(NIR-HA), NIR-labeled-HA-TET (NIR-HA-TET), and NIR-labeled-HA-TCO (NIR-HA-TCO).

First, IR-783 (250 mg, 0.33 mmol) was dissolved in 10 mL dimethylformamide. Sodium azide (30 mg, 0.5 mmol) was then added to the IR-783 solution at room temperature under nitrogen followed by stirring at 65° C. for 24 h. Propargylamine (42.6 mg, 0.66 mmol), copper sulfate (110 mg, 0.66 mmol), and ascorbic acid (240 mg, 1.32 mmol) were added to the IR-783 solution followed by stirring for 24 h at 25° C. The reaction mixture was subsequently dried in a vacuum to produce amine-modified IR-783 (IR-783-NH$_2$).

The carboxyl group of 0.1 g of HA-TET, or HA-TCO in 30 mL DW was activated by adding DMTMM (16 mg, 0.05 mmol). IR-783-NH$_2$ (30 mg, 0.038 mmol) was added to the activated, HA-TET, and HA-TCO solutions, and the mixtures were stirred for 24 h at 25° C. The reaction mixtures were decanted into dialysis tubes with a molecular weight cutoff of 3.5 kDa (Spectrum Laboratories, CA, USA), and they were then dialyzed for 3 days to remove unreacted IR-783-NH$_2$ and DMTMM. The solutions were then freeze-dried at −70° C. for at least 4 days to produce, NIR-HA-TET, and NIR-HA-TCO.

3-2: Preparation of Hyaluronic Acid Hydrogel (Cx-HA) Formulation Containing Stem Cell Recruiting Factor and In Vivo Injection Each of the NIR-HA-TET and NIR-HA-TCO, which were prepared in Example 3-1, was dissolved in 2% physiological saline to have a volume of 20 mg/mL, thereby preparing an aqueous solution, and 1 μg/mL of SP having an amino acid sequence of SEQ ID NO: 1 or SP1 having an amino acid sequence of SEQ ID NO: 2 was added to each solution. After 1-hour stirring, a hyaluronic acid hydrogel solution containing a stem cell recruiting factor was obtained by mixing the mixed solution prepared by stirring each of the solutions using a dual syringe. Each composition is shown in Table 3 below.

TABLE 3

Composition of formulation containing stem cell recruiting factor

| Experimental Group | Composition |
|---|---|
| NIR-labeled Cx-HA | NIR-HA-Tet, NIR-HA-TCO |
| NIR-labeled Cx-HA + SP | NIR-HA-Tet + 1 µg/mL SP, NIR-HA-TCO + 1 µg/mL SP |
| NIR-labeled Cx-HA + SP1 | NIR-HA-Tet + 1 µg/mL SP1, NIR-HA-TCO + 1 µg/mL SP1 |

NIR-labeled Cx-HA was injected into one side of a nude mouse, and NIR-labeled Cx-HA containing a stem cell recruiting factor was injected into the other side thereof, as shown in Table 3.

Example 4

Injection of hMSCs Labeled with Indocyanine Green

To visually confirm the extent of stem cell recruiting of SP1 in the present invention, hMCSs were labeled with indocyanine green and injected into a mouse caudal vein.

First, an indocyanine green (ICG) solution was prepared by dissolving 2 mg of ICG in 200 µL of DMSO, and mixing the resulting solution with 800 µL of a culture medium (DMEM (low-glucose)+10% FBS+1% penicillin-streptomycin). 10 µL of a 10 mg/mL protamine solution, 600 µL of the ICG solution and 600 µL of MEM-α were mixed, and gently stirred for 5 minutes. Afterward, the medium was removed from the flask in which hMSCs were cultured, replaced with 10 mL of a serum-free DMEM (low-glucose) medium, and then incubated for 1 hour at 37° C. under a 5% $CO_2$ condition by adding a protamine/ICG solution.

Subsequently, the medium was removed, and the cells were washed with 10 mL PBS and treated with trypsin, thereby obtaining hMSCs. The hMSCs were prepared to be $1 \times 10^6$ cells/100 µL, and Cx-Ha shown in Example 3 was injected into the caudal veins of nude mice using a 300-gauge syringe (FIG. 3). NIR fluorescence imaging was performed at a predetermined time using FOBI (NeoScience, Suwon, Korea) at 730 nm under conditions of an exposure of 2000 ms and a gain of 5.

Example 5

Observation of In Vivo Migration of hMSCs by SP1

To confirm the extent of promotion of in vivo hMSC migration by SP1 in the present invention, the hMSC-injected nude mice prepared in Example 4 were subjected to NIR fluorescence imaging using FOBI (NeoScience, Suwon, Korea) at 730 nm under conditions of an exposure of 2000 ms and a gain of 5.

In all experimental groups, while fluorescence was not observed in the control (Cx-HA), fluorescence was observed only at an SP or SP1-injected site. As a result of comparing FIGS. 4 (SP) and 5 (SP1), it was confirmed that SP1 exhibited a higher stem cell recruiting activity, which is similar to the result of confirming in vitro stem cell migration.

In addition, as shown in FIG. 6, as a result of quantifying an amount of stem cells moved to the SP or SP1-injected site, it was confirmed that, compared with conventional SP, SP1 exhibits a higher stem cell recruiting activity, and a stem cell recruiting activity maintenance time is longer.

A substance P analog having a progenitor cell or stem cell recruiting activity according to the present invention can have an excellent stem cell migration activity in vitro, compared with substance P, and when the substance P analog is administered in vivo, excellent stem cell recruiting efficiency is exhibited, compared to the conventional substance P. Therefore, the substance P analog can be effectively used in progenitor cell or stem cell recruiting, regeneration or treatment of a damaged organ or tissue, or wound healing.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A polypeptide comprising the amino acid sequence of SEQ ID NO: 1, wherein the polypeptide has progenitor cells or stem cells recruiting activity.

2. The polypeptide of claim 1, wherein the polypeptide is a substance P analog.

3. The polypeptide of claim 1, wherein the progenitor cells or stem cells are endogenous progenitor cells or endogenous stem cells.

4. The polypeptide of claim 3, wherein the endogenous stem cells comprise one or more selected from the group consisting of mesenchymal stem cells (MSCs), corneal stem cells, auditory stem cells, myocardial stem cells and nerve stem cells.

5. A method of recruiting progenitor cells or stem cells in a subject, comprising: administering an effective amount of a composition comprising a polypeptide comprising the amino acid sequence of SEQ ID NO: 1 to the subject.

6. A method of healing a wound of a subject, comprising: administering an effective amount of a composition comprising a polypeptide comprising the amino acid sequence of SEQ ID NO: 1 to the wound site of the subject.

* * * * *

SEQUENCE LISTING

<160> NUMBER OF SEQ ID NOS: 2

<210> SEQ ID NO 1
<211> LENGTH: 11
<212> TYPE: PRT
<213> ORGANISM: Artificial
<220> FEATURE:
<223> OTHER INFORMATION: SP1

<400> SEQUENCE: 1

Arg Ile Ser Pro Gln Gln Arg Asp Ala Leu Ala
1               5                   10

<210> SEQ ID NO 2
<211> LENGTH: 11
<212> TYPE: PRT
<213> ORGANISM: Artificial
<220> FEATURE:
<223> OTHER INFORMATION: Substance P (SP)

<400> SEQUENCE: 2

Arg Pro Lys Pro Gln Gln Phe Phe Gly Leu Met
1               5                   10